(12) United States Patent
Conner et al.

(10) Patent No.: US 11,607,511 B2
(45) Date of Patent: Mar. 21, 2023

(54) INDUCTIVELY-HEATED SUBSTRATE TABLET FOR AEROSOL DELIVERY DEVICE

(71) Applicant: RAI STRATEGIC HOLDINGS, INC., Winston-Salem, NC (US)

(72) Inventors: Billy T. Conner, Clemmons, NC (US); Karen H. Cleckley, Kernersville, NC (US); Thaddeus Jackson, Summerfield, NC (US); Cortney Rasheen Jackson, Colfax, NC (US)

(73) Assignee: NICOVENTURES TRADING LIMITED, London (GB)

( * ) Notice: Subject to any disclaimer, the term of this patent is extended or adjusted under 35 U.S.C. 154(b) by 502 days.

(21) Appl. No.: 16/737,140

(22) Filed: Jan. 8, 2020

(65) Prior Publication Data

US 2021/0205552 A1     Jul. 8, 2021

(51) Int. Cl.
*A24F 40/40*     (2020.01)
*A61M 15/06*     (2006.01)
(Continued)

(52) U.S. Cl.
CPC .......... *A61M 15/06* (2013.01); *A61M 11/042* (2014.02); *A61M 2205/3368* (2013.01); *A61M 2205/3653* (2013.01); *A61M 2205/8206* (2013.01); *H05B 1/0244* (2013.01); *H05B 2203/021* (2013.01)

(58) Field of Classification Search
CPC ........ A24D 1/14; A24F 47/008; A61M 15/06; A61N 11/042
See application file for complete search history.

(56) References Cited

U.S. PATENT DOCUMENTS 2,057,353 A    10/1936   Whittemore, Jr.
2,104,266 A    1/1938   McCormick
(Continued)

FOREIGN PATENT DOCUMENTS

CN     1541577 A    11/2004
CN     2719043 Y    8/2005
(Continued)

OTHER PUBLICATIONS

International Search Report from the corresponding International Application No. PCT/IB2021/050096, dated Mar. 17, 2021.
(Continued)

*Primary Examiner* — Neil Abrams
(74) *Attorney, Agent, or Firm* — Womble Bond Dickinson (US) LLP

(57) ABSTRACT

An aerosol delivery device and a substrate tablet for use with an inductively-heated aerosol delivery device are provided. The aerosol delivery device comprises a control body having a housing, a mouthpiece portion located proximate the housing, a resonant transmitter located in the control body, a control component configured to drive the resonant transmitter, and a substrate tablet receivable in the device. The substrate tablet may comprise a granular substrate material and a susceptor component, the substrate material and the susceptor component may be configured to be formed together, and the susceptor component may be configured to be heated by the resonant transmitter.

24 Claims, 6 Drawing Sheets

Figure 1:
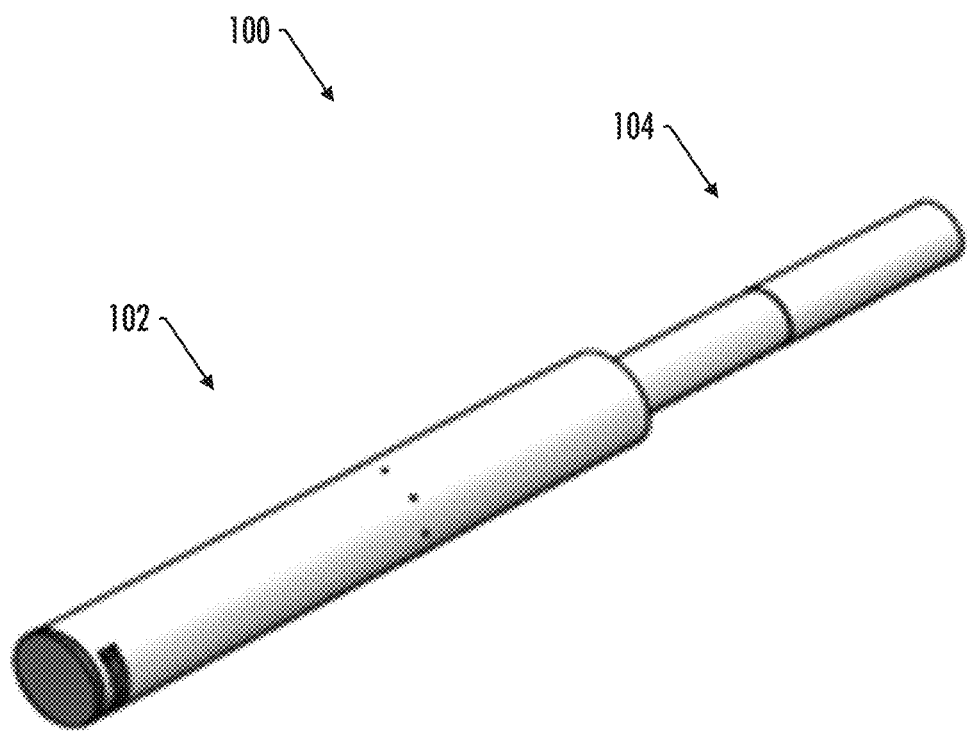

(51) Int. Cl.
*A61M 11/04* (2006.01)
*H05B 1/02* (2006.01)

(56) References Cited

U.S. PATENT DOCUMENTS

| | | |
|---|---|---|
| 3,200,819 A | 8/1965 | Gilbert |
| 4,922,901 A | 5/1990 | Brooks et al. |
| 5,060,671 A | 10/1991 | Counts et al. |
| 5,093,894 A | 3/1992 | Deevi et al. |
| 5,261,424 A | 11/1993 | Sprinkel, Jr. |
| 5,388,574 A | 2/1995 | Ingebrethsen et al. |
| 5,530,225 A | 6/1996 | Hajaligol |
| 5,687,746 A | 11/1997 | Rose et al. |
| 5,726,421 A | 3/1998 | Fleischhauer et al. |
| 5,865,185 A | 2/1999 | Collins et al. |
| 5,894,841 A | 4/1999 | Voges |
| 6,125,853 A | 10/2000 | Susa et al. |
| 6,155,268 A | 12/2000 | Takeuchi |
| 7,117,867 B2 | 10/2006 | Cox et al. |
| 7,832,410 B2 | 11/2010 | Hon |
| 8,314,591 B2 | 11/2012 | Terry et al. |
| 8,365,742 B2 | 2/2013 | Hon |
| 8,499,766 B1 | 8/2013 | Newton |
| 2005/0016550 A1 | 1/2005 | Katase |
| 2006/0196518 A1 | 9/2006 | Hon |
| 2008/0092912 A1 | 4/2008 | Robinson et al. |
| 2009/0095311 A1 | 4/2009 | Hon |
| 2009/0126745 A1 | 5/2009 | Hon |
| 2009/0188490 A1 | 7/2009 | Hon |
| 2009/0272379 A1 | 11/2009 | Thorens et al. |
| 2011/0094523 A1 | 4/2011 | Thorens et al. |
| 2011/0126848 A1 | 6/2011 | Zuber et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0290248 A1 | 12/2011 | Schennum |
| 2012/0111347 A1 | 5/2012 | Hon |
| 2012/0260927 A1 | 10/2012 | Liu |
| 2012/0279512 A1 | 11/2012 | Hon |
| 2013/0037041 A1 | 2/2013 | Worm et al. |
| 2013/0056013 A1 | 3/2013 | Terry et al. |
| 2013/0306084 A1 | 11/2013 | Flick |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2017/0055583 A1* | 3/2017 | Blandino .......... A24D 1/20 |
| 2017/0105452 A1* | 4/2017 | Mironov .......... A24F 40/42 |
| 2018/0295885 A1* | 10/2018 | Rojo-Calderon ..... A24F 40/465 |
| 2018/0317554 A1* | 11/2018 | Kaufman .......... H05B 6/105 |
| 2019/0200677 A1* | 7/2019 | Chong .......... A24F 40/465 |
| 2019/0239555 A1* | 8/2019 | Nicholson .......... A61M 15/06 |
| 2019/0387787 A1* | 12/2019 | Hejazi .......... A24D 1/20 |
| 2020/0120984 A1* | 4/2020 | Rogan .......... A24F 40/44 |
| 2021/0205552 A1* | 7/2021 | Conner .......... A61M 15/06 |
| 2021/0329748 A1* | 10/2021 | Taurino .......... A24F 40/42 |

FOREIGN PATENT DOCUMENTS

| | | |
|---|---|---|
| CN | 201379072 Y | 1/2010 |
| EP | 0 295 122 A2 | 12/1988 |
| EP | 0 845 220 A1 | 6/1998 |
| EP | 1 618 803 A1 | 1/2006 |
| GB | 2469850 A | 11/2010 |
| WO | 2003/034847 A1 | 5/2003 |
| WO | 2004/080216 A1 | 9/2004 |
| WO | 2005/099494 A1 | 10/2005 |
| WO | 2007/131449 A1 | 11/2007 |
| WO | 2017/068093 A1 | 4/2017 |
| WO | 2019/105811 A1 | 6/2019 |

OTHER PUBLICATIONS

Kara et al., "A Review on Manufacturing of Tablets by Using Various Granulation Techniques", Journal of Global Pharma Technology, 2017, pp. 5-10.

* cited by examiner

INDUCTIVELY-HEATED SUBSTRATE TABLET FOR AEROSOL DELIVERY DEVICE

TECHNOLOGICAL FIELD

The present disclosure relates to substrate tablets and aerosol delivery devices and uses thereof for yielding tobacco components or other materials in inhalable form. More particularly, the present disclosure relates to substrate tablets and aerosol delivery devices and systems, such as smoking articles, that utilize electrically-generated heat to heat substrate material, which may be tobacco or a tobacco derived material, preferably without significant combustion, in order to provide an inhalable substance in the form of an aerosol for human consumption.

BACKGROUND

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference in their entireties. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference in its entirety. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference in their entireties.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™ JET™, MAXXQ™ PINK™ and PITBULL™ by SMOKE STIK®, HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd; IQOS™ by Philip Morris International; and GLO™ by British American Tobacco. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™.

Articles that produce the taste and sensation of smoking by electrically heating tobacco or tobacco derived materials have suffered from inconsistent performance characteristics. Accordingly, it is desirable to provide a smoking article that can provide the sensations of cigarette, cigar, or pipe smoking, without substantial combustion, and that does so with advantageous performance characteristics.

BRIEF SUMMARY

In various implementations, the present disclosure provides an aerosol delivery device and a substrate tablet for use with an aerosol delivery device. The present disclosure includes, without limitation, the following example implementations:

An aerosol delivery device comprising a control body having a housing, a mouthpiece portion located proximate the housing, a resonant transmitter located in the control body, a control component configured to drive the resonant transmitter, and at least one substrate tablet receivable in the device, wherein the substrate tablet comprises a granular substrate material and a susceptor component, wherein the substrate material and the susceptor component are formed together, and wherein the susceptor component is configured to be heated by the resonant transmitter.

The aerosol delivery device of any preceding example implementation, or any combination of any preceding example implementations, wherein the substrate tablet is formed by pressing the substrate material and the susceptor component together.

The aerosol delivery device of any preceding example implementation, or any combination of any preceding example implementations, wherein the substrate tablet is formed using a process selected from the group consisting of wet granulation, dry granulation, and direct compression.

The aerosol delivery device of any preceding example implementation, or any combination of any preceding example implementations, wherein the substrate tablet defines a profile shape, and wherein the profile shape of the substrate tablet is substantially round.

The aerosol delivery device of any preceding example implementation, or any combination of any preceding example implementations, wherein the substrate tablet defines a first end surface and a second end surface, and further includes one or more passages extending from the first end surface to the second end surface.

The aerosol delivery device of any preceding example implementation, or any combination of any preceding example implementations, wherein the susceptor component comprises a susceptor ring.

The aerosol delivery device of any preceding example implementation, or any combination of any preceding example implementations, wherein the substrate tablet defines a first end surface and a second end surface, and wherein the susceptor ring is located proximate one of the first or second end surfaces.

The aerosol delivery device of any preceding example implementation, or any combination of any preceding example implementations, wherein the substrate tablet defines a first end surface and a second end surface, and wherein the susceptor ring is located between the first and second end surfaces.

The aerosol delivery device of any preceding example implementation, or any combination of any preceding example implementations, wherein the susceptor component comprises a granular material, and wherein the granular susceptor material is mixed with the substrate material prior to being formed into the tablet.

The aerosol delivery device of any preceding example implementation, or any combination of any preceding example implementations, wherein the susceptor component comprises a shredded material, and wherein the shredded susceptor material is mixed with the substrate material prior to being formed into the substrate tablet.

The aerosol delivery device of any preceding example implementation, or any combination of any preceding example implementations, wherein the susceptor component comprises an open-ended cup defining a cavity therein, and wherein the substrate material is located in the cavity.

The aerosol delivery device of any preceding example implementation, or any combination of any preceding example implementations, wherein the substrate material includes an aerosol precursor composition.

The aerosol delivery device of any preceding example implementation, or any combination of any preceding example implementations, wherein the susceptor component comprises a material selected from a cobalt material, an iron material, a nickel material, a zinc material, a manganese material, a stainless steel material, a ceramic material, a silicon carbide material, a carbon material, and combinations thereof.

The aerosol delivery device of any preceding example implementation, or any combination of any preceding example implementations, wherein the substrate tablet defines a peripheral surface, and wherein a plurality of passages are defined around the peripheral surface.

The aerosol delivery device of any preceding example implementation, or any combination of any preceding example implementations, wherein the control body is configured to receive multiple substrate tablets.

The aerosol delivery device of any preceding example implementation, or any combination of any preceding example implementations, wherein the resonant transmitter is configured to separately heat respective susceptor components of the multiple substrate tablets.

The aerosol delivery device of any preceding example implementation, or any combination of any preceding example implementations, wherein the resonant transmitter is configured to heat multiple respective susceptor components of the multiple substrate tablets.

The aerosol delivery device of any preceding example implementation, or any combination of any preceding example implementations, wherein each of the multiple substrate tablets includes an aerosol precursor composition, and wherein at least two of the multiple substrate tablets have different levels of aerosol precursor composition.

The aerosol delivery device of any preceding example implementation, or any combination of any preceding example implementations, wherein at least two of the multiple substrate tablets have different types of susceptor components.

The aerosol delivery device of any preceding example implementation, or any combination of any preceding example implementations, wherein at least two of the multiple substrate tablets have different shapes.

A substrate tablet for use with an inductively-heated aerosol delivery device, the substrate tablet comprising a granular substrate material, and a susceptor component, wherein the substrate material and the susceptor component are formed together.

The substrate tablet of any preceding example implementation, or any combination of any preceding example implementations, wherein the substrate tablet is formed by pressing the substrate material and the susceptor component together.

The substrate tablet of any preceding example implementation, or any combination of any preceding example implementations, wherein the substrate tablet is formed using a process selected from the group consisting of wet granulation, dry granulation, and direct compression.

The substrate tablet of any preceding example implementation, or any combination of any preceding example implementations, wherein the tablet defines a profile shape, and wherein the profile shape of the tablet is substantially round.

The substrate tablet of any preceding example implementation, or any combination of any preceding example implementations, wherein the tablet defines a first end surface and a second end surface, and further includes one or more passages extending from the first end surface to the second end surface.

The substrate tablet of any preceding example implementation, or any combination of any preceding example implementations, wherein the susceptor component comprises a susceptor ring.

The substrate tablet of any preceding example implementation, or any combination of any preceding example implementations, wherein the tablet defines a first end surface and a second end surface, and wherein the susceptor ring is located proximate one of the first or second end surfaces.

The substrate tablet of any preceding example implementation, or any combination of any preceding example implementations, wherein the tablet defines a first end surface and a second end surface, and wherein the susceptor ring is located between the first and second end surfaces.

The substrate tablet of any preceding example implementation, or any combination of any preceding example implementations, wherein the susceptor component comprises a granular material, and wherein the granular susceptor material is mixed with the substrate material prior to being formed into the tablet.

The substrate tablet of any preceding example implementation, or any combination of any preceding example implementations, wherein the susceptor component comprises a shredded material, and wherein the shredded susceptor material is mixed with the substrate material prior to being formed into the tablet.

The substrate tablet of any preceding example implementation, or any combination of any preceding example implementations, wherein the susceptor component comprises an open-ended cup defining a cavity therein, and wherein the substrate material is located in the cavity.

The substrate tablet of any preceding example implementation, or any combination of any preceding example implementations, wherein the substrate material includes an aerosol precursor composition.

The substrate tablet of any preceding example implementation, or any combination of any preceding example implementations, wherein the susceptor component comprises a material selected from a cobalt material, an iron material, a nickel material, a zinc material, a manganese material, a stainless steel material, a ceramic material, a silicon carbide material, a carbon material, and combinations thereof.

The substrate tablet of any preceding example implementation, or any combination of any preceding example implementations, wherein the tablet defines a peripheral surface, and wherein a plurality of passages are defined around the peripheral surface.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Having thus described the disclosure in the foregoing general terms, reference will now be made to the accompanying drawings, which are not necessarily drawn to scale, and wherein:

FIG. 1 illustrates a perspective view of an aerosol delivery device, according to an example implementation of the present disclosure;

FIG. 2 illustrates a front schematic view of an aerosol delivery device, according to an example implementation of the present disclosure;

FIG. 3A illustrates a perspective view of a substrate tablet, according to an example implementation of the present disclosure;

FIG. 3B illustrates a perspective view of a substrate tablet, according to an example implementation of the present disclosure;

FIG. 3C illustrates a perspective view of a substrate tablet, according to an example implementation of the present disclosure;

FIG. 4 illustrates a front schematic view of the aerosol delivery device, according to an example implementation of the present disclosure;

FIG. 5A illustrates a perspective view of a substrate tablet, according to an example implementation of the present disclosure;

FIG. 5B illustrates a perspective view of a substrate tablet, according to an example implementation of the present disclosure;

FIG. 5C illustrates a front view of a substrate tablet, according to an example implementation of the present disclosure; and FIG. 6 illustrates a front schematic view of an aerosol delivery device, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Aerosol delivery devices according to the present disclosure use electrical energy to heat a material (preferably without combusting the material to any significant degree) to form an inhalable substance. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes may incorporate tobacco and/or components derived from tobacco, and hence deliver tobacco derived components in aerosol form.

Aerosol generating components of aerosol delivery devices of some example implementations may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called "e-cigarettes" or "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure may also be characterized as being vapor-producing articles or medicament delivery articles. Thus, such articles or devices may be adapted so as to provide one or more substances (e.g., flavors and/or pharmaceutical or nutraceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some implementations, the terms "vapor" and "aerosol" may be interchangeable. Thus, for simplicity, the terms "vapor" and "aerosol" as used to describe aspects of the disclosure are understood to be interchangeable unless stated otherwise.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. In some example implementations, an elongated body resembling the shape of a cigarette or cigar can be formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In another example, an aerosol delivery device may be substantially rectangular or have a substantially rectangular cuboid shape. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, another reusable component (e.g., a mouthpiece) or a disposable component (e.g., a disposable flavor-containing cartridge containing aerosol precursor material, flavorant, etc.). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices.

As will be discussed in more detail below, aerosol delivery devices of the present disclosure comprise some combination of a power source (e.g., an electrical power source), at least one control component (e.g., means for actuating, controlling, regulating and ceasing power for heat generation, such as by controlling electrical current flow from the power source to other components of the article—e.g., a microprocessor, individually or as part of a microcontroller), and a heater or heat generation member (e.g., an inductive heating arrangement). Such aerosol delivery devices may be configured to accept one or more substrate tablets that include a substrate material capable of yielding an aerosol upon application of sufficient heat. In some implementations, the aerosol delivery device may include a mouthpiece portion configured to allow drawing upon the aerosol delivery device for aerosol inhalation (e.g., a defined airflow path through the article such that aerosol generated can be withdrawn therefrom upon draw). In some implementations, the mouthpiece portion may be a separate component, while in other implementations the control body may include the mouthpiece portion.

Alignment of the components within the aerosol delivery device of the present disclosure can vary. In specific implementations, the substrate tablet(s) may be positioned proximate a heating member (or a component of a heating arrangement) so as to maximize aerosol delivery to the user. Other configurations, however, are not excluded. Generally, the heating member (or a component of the heating arrangement) may be positioned sufficiently near the substrate tablet(s) so that heat can volatilize the substrate material (as well as, in some implementations, one or more flavorants, medicaments, or the like that may likewise be provided for delivery to a user) and form an aerosol for delivery to the user. When the substrate material is heated, an aerosol is formed, released, or generated in a physical form suitable for inhalation by a user. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device of various implementations may incorporate a power source (e.g., a battery or other electrical power source) to provide current flow sufficient to provide various functionalities to the aerosol delivery device, such as powering of a heating member, powering of an induction coil, powering of control systems, powering of indicators, and the like. The power source can take on various implementations. In some implementations, the power source is able to deliver sufficient power to rapidly activate the heating source to provide for aerosol formation and power the aerosol delivery device through use for a desired duration of time. The power source may be sized to fit conveniently within the aerosol delivery device so that the aerosol delivery device can be easily handled. Additionally, in some implementations, a power source may be of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

As noted, aerosol delivery devices may be configured to heat a substrate material of one or more substrate tablets to produce an aerosol. In some implementations, the aerosol delivery devices may comprise heat-not-burn devices, configured to heat an extruded structure and/or substrate, a substrate material associated with an aerosol precursor composition, tobacco and/or a tobacco-derived material (i.e., a material that is found naturally in tobacco that is isolated directly from the tobacco or synthetically prepared) in a solid or liquid form (e.g., beads, shreds, a wrap, a fibrous sheet or paper), or the like. Such aerosol delivery devices may include so-called electronic cigarettes.

In the depicted implementations, an inductive heating arrangement is used. In various implementations, the inductive heating arrangement may comprise a resonant transmitter and a resonant receiver (e.g., one or more susceptors or susceptor components). In such a manner, operation of the aerosol delivery device may require directing alternating current to the resonant transmitter to produce an oscillating magnetic field in order to induce eddy currents in the resonant receiver. In various implementations, the resonant receiver may be part of a substrate tablet (e.g., mixed with the substrate material and/or disposed proximate the substrate material of a substrate tablet). This alternating current causes the resonant receiver to generate heat and thereby creates an aerosol from the substrate material. Examples of various inductive heating methods and configurations are described in U.S. Pat. App. Pub. No. 2019/0124979 to Sebastian et al., which is incorporated by reference herein in its entirety. Further examples of various induction-based control components and associated circuits are described in U.S. Pat. App. Pub. No. 2018/0132531, and U.S. Patent App. Pub. No. 2017/0202266 to Sur et al., each of which is incorporated herein by reference in its entirety. It should be noted that although the depicted implementations describe a single resonant transmitter, in other implementations, there may be multiple independent resonant transmitters, including, for example, implementations having segmented inductive heating arrangements.

As noted, in some implementations a change in current in the resonant transmitter (e.g., an induction coil), as directed thereto from the power source by the control component (e.g., via a driver circuit) may produce an alternating electromagnetic field that penetrates the susceptor component, thereby generating electrical eddy currents within the susceptor component. In some implementations, the alternating electromagnetic field may be produced by directing alternating current to the resonant transmitter. In some implementations, the control component may include an inverter or inverter circuit configured to transform direct current provided by the power source to alternating current that is provided to the resonant transmitter. As such, in some implementations a resonant transmitter and a substrate tablet may be positioned proximate each other to heat the substrate tablet or a portion thereof (e.g., the substrate material of the substrate tablet) by inductive heating. As will be described in more detail below, a portion of the inductive heating arrangement may be positioned in the control body and a portion of the inductive heating arrangement may be positioned in the substrate tablet.

The eddy currents flowing in the susceptor component may generate heat through the Joule effect, wherein the amount of heat produced is proportional to the square of the electrical current times the electrical resistance of the material of the susceptor component. For implementations wherein the susceptor component comprises ferromagnetic materials, heat may also be generated by magnetic hysteresis losses. Several factors may contribute to the temperature rise of the susceptor component including, but not limited to, proximity to the resonant transmitter, distribution of the magnetic field, electrical resistivity of the material of the susceptor component, saturation flux density, skin effects or depth, hysteresis losses, magnetic susceptibility, magnetic permeability, and dipole moment of the material.

FIG. 1 illustrates a perspective view an aerosol delivery device 100, according to an example implementation of the present disclosure. In the depicted implementation, the aerosol delivery device 100 includes a control body 102 and a mouthpiece portion 104. In various implementations, the mouthpiece portion 104 and the control body 102 can be permanently or detachably aligned in a functioning relationship. In this regard, FIG. 1 illustrates the aerosol delivery device 100 with a removable mouthpiece portion 104 coupled with the control body 102. Various mechanisms may connect the mouthpiece portion 104 to the control body 102 to result in a threaded engagement, a press-fit engagement, an interference fit, a sliding fit, a magnetic engagement, or the like. In various implementations, the control body 102 and/or the mouthpiece portion 104 of the aerosol delivery device 100 may be substantially rod-like, substantially tubular shaped, substantially rectangular or rectangular cuboidal shaped, or substantially cylindrically shaped. In other implementations, the control body may take another hand-held shape, such as a small box shape, various pod mod (e.g., all-in-one) shapes, or a fob-shape.

In specific implementations, one or both of the control body and mouthpiece portion may be referred to as being disposable or as being reusable. As will be described in more detail below, the control body is configured to receive one or more substrate tablets. In various implementations, the substrate tablets may be referred to as being disposable. In some implementations, the entire device may be characterized as being disposable in that the control body may be configured for only a limited number of uses (e.g., until a battery power component no longer provides sufficient power to the article) with a limited number of substrate tablets and, thereafter, the entire device, including the control body, may be discarded. In other implementations, the control body may have a replaceable battery such that the control body may be reused through a number of battery exchanges and with many substrate tablets. Similarly, the device may be rechargeable and thus may be combined with any type of recharging technology.

For example, the control body may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the mouthpiece portion may comprise a single-use device. A single use component for use with a control body is disclosed in U.S. Pat. No. 8,910,639 to Chang et al., which is incorporated herein by reference in its entirety. In some implementations, the control body may be inserted into and/or coupled with a separate charging station for charging a rechargeable battery of the device. In some implementations, the charging station itself may include a rechargeable power source that recharges the rechargeable battery of the device.

Figure 2:
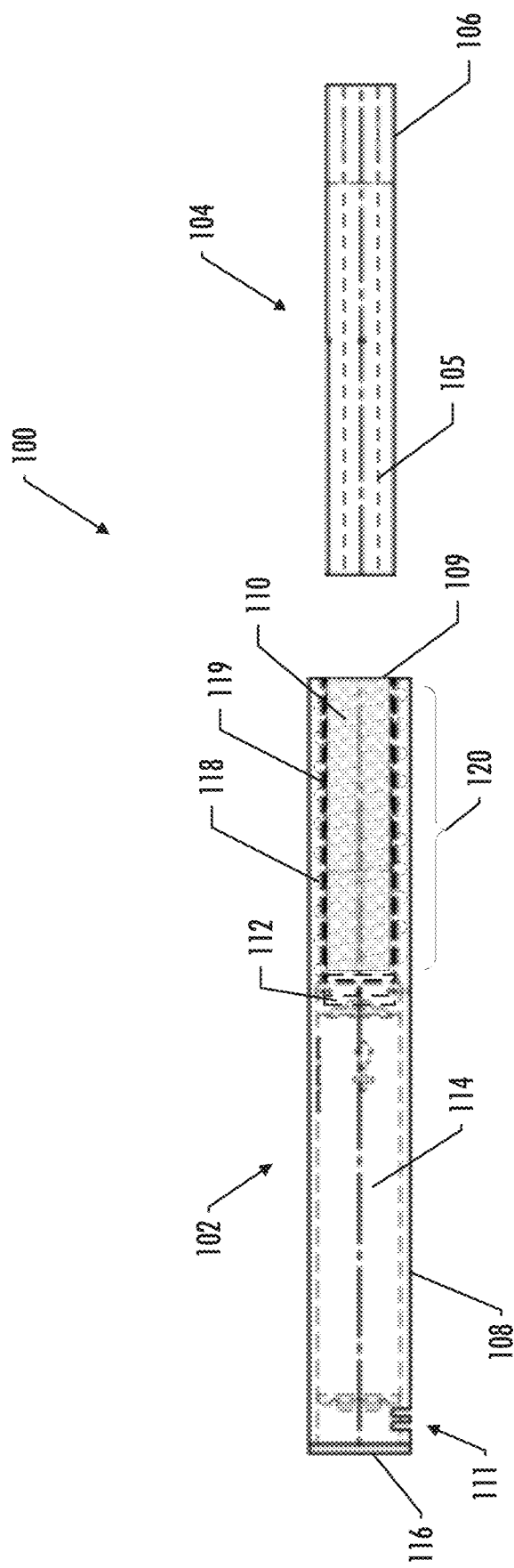

FIG. 2 illustrates a front schematic view of an aerosol delivery device, according to an example implementation of the present invention. In particular, FIG. 2 illustrates the aerosol delivery device 100 of FIG. 1. In the depicted implementation, the mouthpiece portion 104 is attachable and removable from the control body 102 and includes an aerosol passage 105 disposed therethrough. In the depicted implementation, the mouthpiece portion 104 also includes a filter 106, which, for example, may be made of a cellulose acetate or polypropylene material. In various implementations, the filter 106 may provide filtering capacity, if desired, and/or provide resistance to draw. In the depicted implementation, the filter 106 is integral with the mouthpiece portion 104. In other implementations, however, the filter may be separate from the mouthpiece portion. In some implementations, the filter may comprise discrete segments. For example, some implementations may include a segment providing filtering, a segment providing draw resistance, a hollow segment providing a space for the aerosol to cool, a segment providing increased structural integrity, other filter segments, or any one or any combination of the above. Some implementations need not include a filter. In various implementations other components may exist in the mouthpiece portion. For example, in some implementations one or any combination of the following may be included in the mouthpiece portion: an air gap; phase change materials for cooling air; flavor releasing media; ion exchange fibers capable of selective chemical adsorption; aerogel particles as filter medium; and other suitable materials.

As noted above, various implementations of the present disclosure employ an inductive heating arrangement to heat one or more substrate tablets received in the device. The inductive heating arrangement may comprise at least one resonant transmitter and at least one resonant receiver (hereinafter also referred to as a susceptor or a susceptor component). In various implementations, one or both of the resonant transmitter and the resonant receiver may be located in the control body and/or the substrate tablet. As will be described in more detail below, the substrate tablet includes an integral resonant receiver. Examples of additional possible components are described in U.S. Pat. App. Pub. No. 2019/0124979 to Sebastian et al., which is incorporated herein by reference in its entirety.

Referring back to FIG. 2, the control body 102 of the depicted implementation may comprise a housing 108 that includes an opening 109 defined on one end thereof, a flow sensor 111 (e.g., a puff sensor or pressure switch), a control component 112 (e.g., a microprocessor, individually or as part of a microcontroller, a printed circuit board (PCB) that includes a microprocessor and/or microcontroller, etc.), a power source 114 (e.g., a battery, which may be rechargeable, and/or a rechargeable supercapacitor), and an end cap that, in some implementations, may include an indicator 116 (e.g., a light emitting diode (LED)).

Some examples of possible power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties. With respect to the flow sensor 111, some representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947, 874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety. In one implementation, the indicator 116 may comprise one or more light emitting diodes, quantum dot-based light emitting diodes or the like. The indicator 116 can be in communication with the control component 112 and be illuminated, for example, when a user draws on the mouthpiece portion 104, when coupled to the control body 102, as detected by the flow sensor 120.

In some implementations, an input element may be included with the aerosol delivery device (and may replace or supplement an airflow or pressure sensor). The input may be included to allow a user to control functions of the device and/or for output of information to a user. Any component or combination of components may be utilized as an input for controlling the function of the device. For example, one or more pushbuttons may be used as described in U.S. Pub. No. 2015/0245658 to Worm et al., which is incorporated herein by reference in its entirety. Likewise, a touchscreen may be used as described in U.S. Pat. App. Pub. No. 2016/0262454, to Sears et al., which is incorporated herein by reference in its entirety. As a further example, components adapted for gesture recognition based on specified movements of the aerosol delivery device may be used as an input. See U.S. Pat. App. Pub. No. 2016/0158782 to Henry et al., which is incorporated herein by reference in its entirety. As still a further example, a capacitive sensor may be implemented on the aerosol delivery device to enable a user to provide input, such as by touching a surface of the device on which the capacitive sensor is implemented.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Other suitable current actuation/deactuation mechanisms may include a temperature actuated on/off switch or a lip pressure actuated switch, or a touch sensor (e.g., capacitive touch sensor) configured to sense contact between a user (e.g., mouth or fingers of user) and one or more surfaces of the aerosol delivery device. An example mechanism that can provide such puff-actuation capability includes a Model 163PC01D36 silicon sensor, manufactured by the MicroSwitch division of Honeywell, Inc., Freeport, Ill. With such sensor, the heating member may be activated rapidly by a change in pressure when the user draws on the device. In addition, flow sensing devices, such as those using hot-wire anemometry principles, may be used to cause the energizing of the heating assembly sufficiently rapidly after sensing a change in airflow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. In some implementations, a pressure-sensing tube or other passage providing fluid connection between the puff actuated switch and substrate tablet may be included in the housing so that pressure changes during draw are readily identified by the switch. Other example puff actuation devices that may be useful according to the present disclosure are disclosed in U.S. Pat. Nos. 4,922,901, 4,947,874, and 4,947,874, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

As noted above, the heating member of the depicted implementation comprises an inductive heating arrangement. In the implementation depicted in FIG. 2, the control body 102 includes a resonant transmitter and the substrate tablet includes a resonant receiver (e.g., one or more susceptor components), which together facilitate heating of at least a portion of the substrate tablet (e.g., a substrate material of the substrate tablet). It should be noted that the term "tablet" as used herein should not be interpreted as a limitation on size and/or shape. For example, in some implementations the substrate tablet may have a non-circular profile shape and/or a non-cylindrical overall shape. Although in various implementations the substrate tablet may have a variety of forms, in the depicted implementation the substrate tablet 110 comprises a combination of a substrate material and a susceptor component. Although in various implementations the resonant transmitter may have a variety of forms, in the depicted implementation the resonant transmitter comprises an induction coil 118 (such as, but not limited to, a helical coil) that surrounds a support cylinder 119, although in other implementations there need not be a support cylinder. In various implementations, the resonant transmitter may be made of one or more conductive materials, including, for example, silver, gold, aluminum, brass, zinc, iron, nickel, and alloys of thereof, conductive ceramics e.g., yttrium-doped zirconia, indium tin oxide, yttrium doped titanate, etc, and any combination of the above. In the illustrated implementation, the induction coil 118 is made of a conductive metal material, such as copper. In further implementations, the induction coil may include a non-conductive insulating cover/wrap material. Such materials may include, for example, one or more polymeric materials, such as epoxy, silicon rubber, etc., which may be helpful for low temperature applications, or fiberglass, ceramics, refractory materials, etc., which may be helpful for high temperature applications.

In the depicted implementation, the aerosol delivery device 100 defines a receiving compartment 120, which is configured to receive the substrate tablet 110 and is defined proximate the opening 109 of the control body 102. In some implementations, such as the depicted implementation, the receiving compartment may comprise a receiving chamber. In other implementations, however, the receiving compartment may have other forms. For example, in some implementations, the receiving compartment may comprise a rotatable door, a siding tray, etc. As will be discussed in more detail below, in some implementations the receiving compartment may be configured to receive a single substrate tablet. In other implementations, the receiving compartment may be configured to receive multiple (e.g., two or more) substrate tablets. In still other implementations, the same receiving compartment may be configured to receive a single substrate tablet or multiple substrate tablets. In various implementations, the shape of the receiving compartment may be configured to accommodate one or more different profile shapes of a substrate tablet. For example, in some implementations in which the substrate tablet has a substantially round profile shape, the receiving compartment may have a substantially cylindrical shape, etc. It should be noted that while in the depicted implementation the receiving compartment 120 is located in the control body 102 of the aerosol delivery device 100, in other implementations the receiving compartment may be located in the mouthpiece portion, which may be separate from the control body. In such a manner, receiving compartment of the mouthpiece portion may be configured to receive a single substrate tablet and/or multiple substrate tablets.

Although not depicted in the figures, the housing 108 may include one or more apertures therein for allowing entrance of ambient air to be directed into the device (such as, for example, through the substrate tablet(s) contained therein). Thus, when a user draws on the mouthpiece portion 104, air may be drawn into the receiving compartment 120 and be drawn through the substrate tablet(s) for inhalation by the user.

In the depicted implementation, the resonant transmitter 118 extends proximate an engagement end of the housing 108, and may be configured to substantially surround at least a portion of the receiving compartment 120, which is configured to receive one or more substrate tablets. In the depicted implementation, the induction coil 118 defines a generally tubular configuration. In some implementations, the support cylinder 119 may also define a tubular configuration and may be configured to support the induction coil 118 such that the induction coil 118 does not contact with the substrate tablets. As such, the support cylinder 119 may comprise a nonconductive material, which may be substantially transparent to an oscillating magnetic field produced by the induction coil 118. In various implementations, the induction coil 118 may be imbedded in, or otherwise coupled to, the support cylinder 119. In the illustrated implementation, the induction coil 118 is engaged with an outer surface of the support cylinder 119; however, in other implementations, the coil may be positioned at an inner surface of the support cylinder, be fully imbedded in the support cylinder, or have some other configuration.

As noted above, in various implementations of the present invention the substrate tablet includes a substrate material and a susceptor component. In various implementations, the substrate material and the susceptor component are configured to be formed together (such as, for example, by being compressed and/or molded) into a substrate tablet. In such a manner, the substrate material and the susceptor component may first be combined and then subsequently formed into a substrate tablet. In some implementations, this may comprise mixing the substrate material and the susceptor component together and then compressing and/or molding the substrate material and susceptor component into the substrate tablet. For example, in some implementations the substrate material may comprise a granular material (including, but not limited to, shreds, grains, beads, particles etc.) and the susceptor component may comprise a granular material (including, but not limited to, shreds, grains, beads, particles etc.). In such implementations, the granular substrate material and the granular susceptor component may be mixed together (with or without additional additives) and then introduced into a tableting machine, tablet press, and/or other molding device (which may include one or more feeders, dies, punches, and/or compression components) that is configured to compress the mixture into one or more substrate tablets. In other implementations, the susceptor component may comprise a substantially solid structure (including, but not limited to, a disk, ring, cup, cap, etc.), which may be combined with the substrate material to form a substrate tablet. For example, in some implementations having substantially solid susceptor components the substrate tablet may be formed as described above (e.g., via compression and/or molding) with the susceptor component being combined with the substrate material at some point during or after the process.

In various implementations, a substrate tablet may be made in a variety of different ways. For example, in some implementations one or more substrate tablets may be made via wet granulation. In other implementations, one or more substrate tablets may be made via dry granulation. In other implementations, one or more substrate tablets may be made via direct compression. In some implementations, a wet granulation process may comprise one or any combination of the following steps: providing a substrate material and a susceptor component, mixing the substrate material and the substrate component, sifting the substrate material and the susceptor component, preparing and introducing a granulating fluid, granulating the mixture, screening the wet granulated mixture, drying the wet granulated mixture, milling the dried mixture, blending the milled resultant with one or more lubricants, and compressing the resultant into a substrate tablet. In some implementations, a dry granulation process may comprise one or any combination of the following steps: providing a substrate material and a susceptor component, mixing the substrate material and the susceptor component, sifting the substrate material and the susceptor component, slugging the substrate material and the susceptor component (e.g., pre-compressing the substrate material and susceptor component into slugs), screening the slugs, granulating the slugs, and compressing the granulated resultant into a substrate tablet. In other implementations, a dry granulating process may comprise one or any combination of the following steps: providing a substrate material and a susceptor component, mixing the substrate material and the susceptor component, sifting the substrate material and the susceptor component, passing the substrate material and the susceptor component through high-pressure rollers, collecting flakes and/or granules, milling the flakes and/or granulates, and compressing the milled flakes and/or granules into a substrate tablet. In some implementations, a direct compression process may comprise one or any combination of the following steps: providing a substrate material and a susceptor component, mixing the substrate material and susceptor component, sifting the substrate material and the susceptor component, blending the substrate material and the susceptor component, and compressing the resultant into a substrate tablet.

Figure 3A:
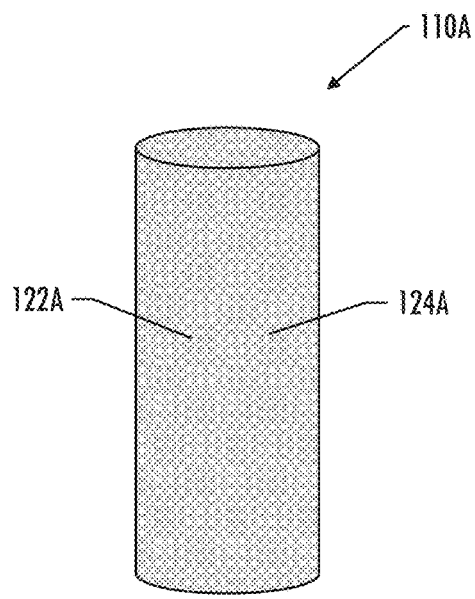
Figure 3B:
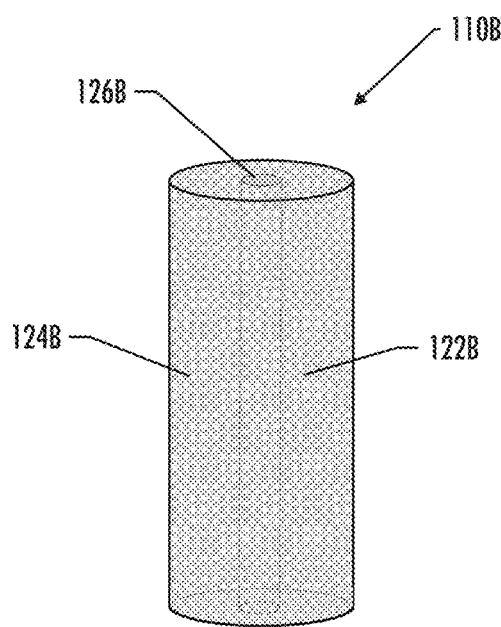
Figure 3C:
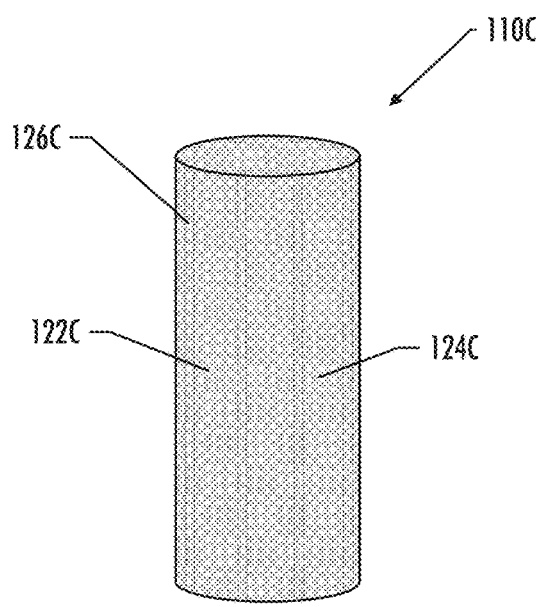

FIGS. 3A-3C show three non-limiting examples of substrate tablets 110A, 110B, and 110C, according some example implementations of the present invention. Although a substrate tablet of the present invention may have a variety of different profile shapes (e.g., as viewed from the top in the figures), including, but not limited to, square, rectangular, oval, almond, trianglular, pentagon, diamond, capsule, etc., in the implementations depicted in FIGS. 3A-3C the tablets 110A, 110B, 110C have round profile shapes, which result in a substantially cylindrical overall shapes. Although other implementations may differ, in the implementations depicted in FIGS. 3A-3C the substrate tablets 110A, 110B, 110C comprise granular substrate materials 122A, 122B, 122C that are combined with granular susceptor components 124A, 124B, 124C.

In various implementations, the substrate material may comprise a tobacco material, a non-tobacco material, or a combination thereof. In some implementations, the substrate material may include, or may essentially be comprised of one or more of a tobacco, a tobacco related material, glycerin, water, a binder material, a diluent, and/or fillers and firming agents, such as, for example, calcium carbonate, rice flour, corn flour, etc. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass. Some implementations may include diluents, which may include, for example, starches or partially pregelatinized starches, highly functional polyols, soluble diluents including maltodextrins, dried glucose syrups, dextrose monohydrate, and dextrose anhydrous, and microcrystalline cellulose (MCC). Other examples include lactose, spray dried lactose, Pvpk30 (Pearlitol SD200 and 25C), sorbitol, dibasic calcium phosphate dehydrate, calcium sulphate dehydrate, etc.

In some implementations, the substrate material may, at some point in the process (e.g., prior to granulation), comprise an extruded material. An example of an extruded substrate material is described in U.S. Pat. App. Pub. No. 2012/0042885 to Stone et al., which is incorporated herein by reference in its entirety. In yet another implementation, the substrate material may begin as an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings. In other implementations, the extruded material may have two or more sectors, such as, for example, an extrudate with a wagon wheel-like cross section.

Additionally or alternatively, the substrate material may, at some point in the process, comprise an extruded structure and/or a substrate that includes or essentially is comprised of tobacco, glycerin, water, and/or binder material. Some example tobacco and/or tobacco related materials that may be suitable are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In other implementations, the substrate material may comprise a blend of flavorful and aromatic tobaccos in cut filler form. In another implementation, the substrate material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entireties. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in their entirety. For example, a reconstituted tobacco material may include a sheet-like material containing tobacco and/or tobacco-related materials. As such, in some implementations, the substrate material may be first formed from a wound roll of a reconstituted tobacco material. In another implementation, the substrate material may be formed from shreds, strips, and/or the like of a reconstituted tobacco material. In another implementation, the tobacco sheet may comprise a crimped sheet of reconstituted tobacco material. In some implementations, the substrate material may comprise overlapping layers (e.g., a gathered web), which may, or may not, include heat conducting constituents. Other examples include a series of overlapping layers (e.g., gathered webs) of an initial substrate sheet formed by the fibrous filler material, aerosol forming material, and plurality of heat conducting constituents are described in U.S. Pat. App. Pub. No. 2019/0261685 to Sebastian, et al., which is incorporated herein by reference in its entirety.

In some implementations, the substrate material may comprise a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, the substrate material may include a plurality of microcapsules each formed into a hollow cylindrical shape. In some implementations, the substrate material may include a binder material configured to maintain the structural shape and/or integrity of the plurality of microcapsules formed into the hollow cylindrical shape.

Tobacco employed in one or more of the substrate materials may include, or may be derived from, tobaccos such as flue-cured tobacco, burley tobacco, Oriental tobacco, Maryland tobacco, dark tobacco, dark-fired tobacco and *Rustica* tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/0255965 to Perfetti et al.; PCT Pub. No. WO 02/37990 to Bereman; and Bombick et al., *Fund. Appl. Toxicol.*, 39, p. 11-17 (1997); the disclosures of which are incorporated herein by reference in their entireties.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

In some implementations, flame/burn retardant materials and other additives may be included within the substrate material and may include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior. Other examples include diammonium phosphate and/or another salt configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Example casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

In various implementations, one or more of the substrate materials may have an aerosol precursor composition associated therewith. For example, in some implementations the aerosol precursor composition may comprise one or more different components, such as polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference their entireties. In some aspects, a substrate material may produce a visible aerosol upon the application of sufficient heat thereto (and cooling with air, if necessary), and the substrate material may produce an aerosol that is "smoke-like." In other aspects, the substrate material may produce an aerosol that is substantially non-visible but is recognized as present by other characteristics, such as flavor or texture. Thus, the nature of the produced aerosol may be variable depending upon the specific components of the aerosol delivery component. The aerosol may be chemically simple relative to the chemical nature of the smoke produced by burning tobacco.

In some implementations, the aerosol precursor composition may comprise one or more humectants such as, for example, propylene glycol, glycerin, and/or the like. In various implementations, the amount of the aerosol precursor composition that is used within the aerosol delivery device may be such that the aerosol delivery device exhibits acceptable sensory and organoleptic properties, and desirable performance characteristics. For example, in some implementations the aerosol precursor composition (such as, for example, glycerin and/or propylene glycol), may be employed in order to provide for the generation of a visible mainstream aerosol that in many regards resembles the appearance of tobacco smoke. For example, the amount of aerosol precursor composition incorporated into the substrate material of the smoking article may be in the range of about 4.5 grams or less, 3.5 grams or less, about 3 grams or less, about 2.5 grams or less, about 2 grams or less, about 1.5 grams or less, about 1 gram or less, or about 0.5 gram or less. It should be noted, however, that in other implementations values outside of these ranges are possible.

Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference in their entireties. In some aspects, a substrate material may produce a visible aerosol upon the application of sufficient heat thereto (and cooling with air, if necessary), and the substrate material may produce an aerosol that is "smoke-like." In other aspects, the substrate material may produce an aerosol that is substantially non-visible but is recognized as present by other characteristics, such as flavor or texture. Thus, the nature of the produced aerosol may be variable depending upon the specific components of the aerosol delivery component. In various implementations, the substrate material may be chemically simple relative to the chemical nature of the smoke produced by burning tobacco.

In some implementations, the aerosol precursor composition, also referred to as a vapor precursor composition or "e-liquid," may comprise a variety of components including, by way of example, a polyhydric alcohol (e.g., glycerin, propylene glycol, or a mixture thereof), nicotine, tobacco, tobacco extract, and/or flavorants. Some possible types of aerosol precursor components and formulations are set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference in their entireties. Other aerosol precursors that may be employed include the aerosol precursors that have been incorporated in VUSE® products by R. J. Reynolds Vapor Company, the BLU' products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also possible are the so-called "smoke juices" for electronic cigarettes that have been available from Johnson Creek Enterprises LLC. Still further examples of possible aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the substrate material is such that the aerosol generating piece provides acceptable sensory and desirable performance characteristics. For example, it is desired that sufficient amounts of aerosol forming material be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 0.5 ml or more, about 1 ml or more, about 2 ml or more, about 5 ml or more, or about 10 ml or more of the aerosol precursor composition may be included.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally include one or more active ingredients including, but not limited to, a nicotine component, botanical ingredients (e.g., lavender, peppermint, chamomile, basil, rosemary, ginger, cannabis, ginseng, maca, hemp, eucalyptus, rooibos, fennel, citrus, cloves, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C, and/or cannabinoids, such as tetrahydrocannabinol (THC) and cannabidiol (CBD)). The particular percentages and choice of ingredients will vary depending upon the desired flavor, texture, and other characteristics. Example active ingredients would include any ingredient known to impact one or more biological functions within the body, such as ingredients that furnish pharmacological activity or other direct effect in the diagnosis, cure, mitigation, treatment, or prevention of disease, or which affect the structure or any function of the body of humans or other animals (e.g., provide a stimulating action on the central nervous system, have an energizing effect, an antipyretic or analgesic action, or an otherwise useful effect on the body).

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. For example, some flavoring agents may be applied to, or incorporated within, the substrate material and/or those regions of the smoking article where an aerosol is generated. In some implementations, such agents may be supplied directly to a heating cavity or region proximate to the heat source or are provided with the substrate material. Example flavoring agents may include, for example, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, may also be suitable to be employed.

Flavoring agents may also include acidic or basic characteristics (e.g., organic acids, such as levulinic acid, succinic acid, pyruvic acid, and benzoic acid). In some implementations, flavoring agents may be combinable with the elements of the substrate material if desired. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. Any of the materials, such as flavorings, casings, and the like that may be useful in combination with a tobacco material to affect sensory properties thereof, including organoleptic properties, such as described herein, may be combined with the substrate material. Organic acids particularly may be able to be incorporated into the substrate material to affect the flavor, sensation, or organoleptic properties of medicaments, such as nicotine, that may be able to be combined with the substrate material. For example, organic acids, such as levulinic acid, lactic acid, and pyruvic acid, may be included in the substrate material with nicotine in amounts up to being equimolar (based on total organic acid content) with the nicotine. Any combination of organic acids may be suitable. For example, in some implementations, the substrate material may include approximately 0.1 to about 0.5 moles of levulinic acid per one mole of nicotine, approximately 0.1 to about 0.5 moles of pyruvic acid per one mole of nicotine, approximately 0.1 to about 0.5 moles of lactic acid per one mole of nicotine, or combinations thereof, up to a concentration wherein the total amount of organic acid present is equimolar to the total amount of nicotine present in the substrate material. Various additional examples of organic acids that may be employed to produce a substrate material are described in U.S. Pat. App. Pub. No. 2015/0344456 to Dull et al., which is incorporated herein by reference in its entirety.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In some implementations, the substrate material may include other materials having a variety of inherent characteristics or properties. For example, the substrate material may include a plasticized material or regenerated cellulose in the form of rayon. As another example, viscose (commercially available as VISIL®), which is a regenerated cellulose product incorporating silica, may be suitable. Some carbon fibers may include at least 95 percent carbon or more. Similarly, natural cellulose fibers such as cotton may be suitable, and may be infused or otherwise treated with silica, carbon, or metallic particles to enhance flame-retardant properties and minimize off-gassing, particularly of any undesirable off-gassing components that would have a negative impact on flavor (and especially minimizing the likelihood of any toxic off-gassing products). Cotton may be treatable with, for example, boric acid or various organo-phosphate compounds to provide desirable flame-retardant properties by dipping, spraying or other techniques known in the art. These fibers may also be treatable (coated, infused, or both by, e.g., dipping, spraying, or vapor-deposition) with organic or metallic nanoparticles to confer the desired property of flame-retardancy without undesirable off-gassing or melting-type behavior.

As noted above, substrate tablets in accordance with various embodiments include one or more susceptor components configured to be heated by the resonant transmitter. In various implementations, one or more of the susceptor components may be made of a ferromagnetic material including, but not limited to, cobalt, iron, nickel, zinc, manganese, and any combinations thereof. In other implementations, one or more of the susceptor components may be made of other materials, including, for example, other metal materials such as aluminum or stainless steel, as well as ceramic materials such as silicon carbide, carbon materials, and any combinations of any of the materials described above. In still other implementations, one or more of the susceptor components may be made of other conductive materials including metals such as copper, alloys of conductive materials, or other materials with one or more conductive materials imbedded therein. In some implementations, the susceptor component may comprise a granulated susceptor component, including, but not limited to a shredded susceptor material. In other implementations, a granulated susceptor component may comprise susceptor particles, susceptor beads, etc.

As noted above, in various implementations an aerosol delivery device of the present invention may receive a single substrate tablet and/or a plurality (e.g., two or more) substrate tablets. The implementation depicted in FIG. 2 is configured to receive a single substrate tablet. FIGS. 3A-3B illustrate example implementations of some substrate tablets that may be received by the aerosol delivery device of FIG. 2. For example, FIG. 3A illustrates a substrate tablet 110A comprising a granulated substrate material 122A (including any one or any combination of substrate materials described above) and a granulated susceptor component 124A, which are together formed into a tablet. In the depicted implementation, the substrate tablet 110A has a substantially circular profile shape (e.g., as viewed from the top of FIG. 3A) that forms a substantially cylindrical overall shape and is configured to be porous so as to allow airflow and/or aerosol flow therethrough.

In some implementations, a substrate tablet of the present invention may include one or more tablet passages extending from one end surface to the other end surface through the tablet. FIG. 3B illustrates an example of such a tablet. In the depicted implementation, the substrate tablet 110B is similar in shape to the substrate tablet 110A of FIG. 3A. For example, substrate tablet 110B has a substantially cylindrical overall shape that forms a substantially circular profile shape (e.g., as viewed from the top of FIG. 3B). In the depicted implementation, the substrate tablet 110B comprises a granulated substrate material 122B (including any one or any combination of substrate materials described above) and a granulated susceptor component 124B, which together are formed into a tablet. The substrate tablet 110B of the depicted implementation further includes a tablet passage 126B, configured to allow air and/or aerosol flow therethrough. FIG. 3C illustrates another example of a substrate tablet having one or more passages. In the depicted implementation, the substrate tablet 110C is similar in shape as the substrate tablet 110A of FIG. 3A. For example, substrate tablet 110C has a substantially circular profile shape (e.g., as viewed from the top of FIG. 3C) that forms a substantially cylindrical overall shape. In the depicted implementation, the substrate tablet 110C comprises a granulated substrate material 122C (including any one or any combination of substrate materials described above) and a granulated susceptor component 124C, which are together formed into a tablet. The substrate tablet 110C of the depicted implementation further includes a plurality of tablet passages 126C, configured to allow air and/or aerosol flow therethrough. Although other configurations are possible, in the depicted implementation there are six tablet passages 126C that are substantially evenly spaced around a periphery of the tablet 310C. In other implementations, there may be more or less tablet passages, and the tablet passages need not be evenly spaced or located on the periphery of the tablet.

Figure 4:
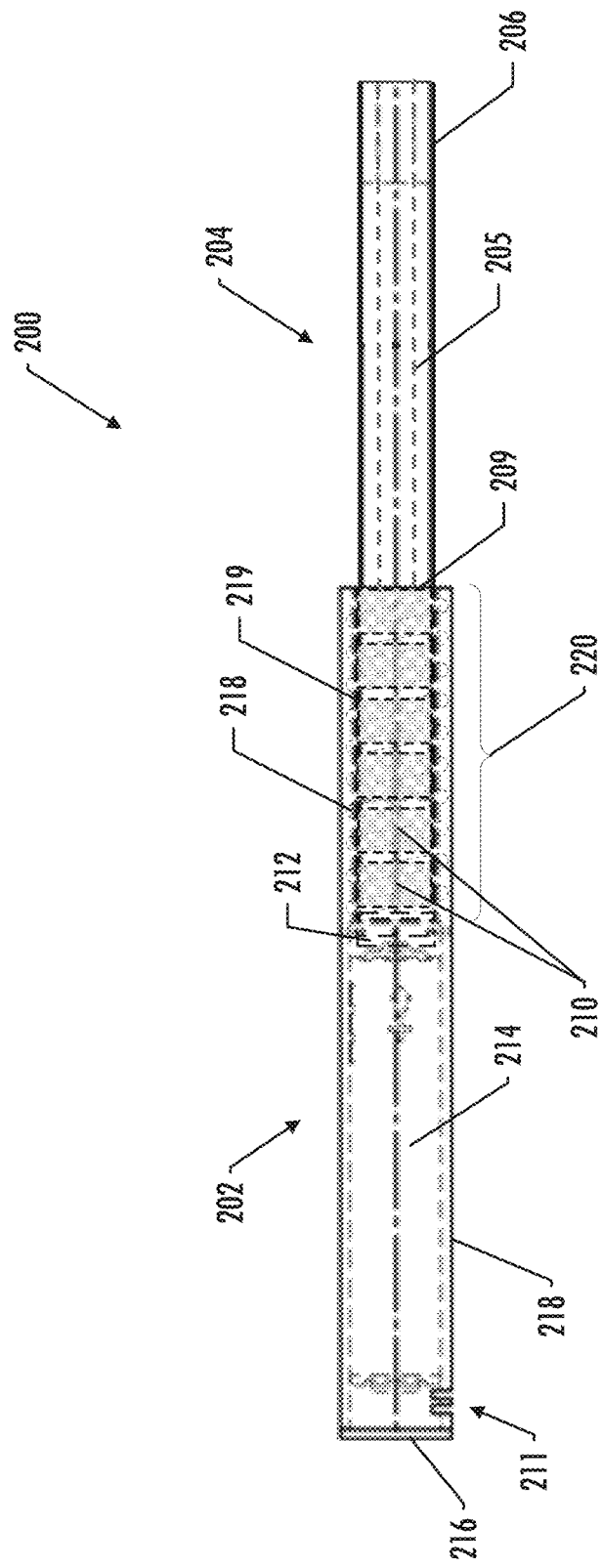

FIG. 4 illustrates a front schematic view of an aerosol delivery device 200, according to another example implementation of the present invention. In particular, FIG. 4 illustrates the aerosol delivery device 200 including a mouthpiece portion 204 that is attachable and removable from a control body 202. In the depicted implementation, the mouthpiece portion 204 includes an aerosol passage 205 disposed therethrough. In the depicted implementation, the mouthpiece portion 204 also includes a filter 206, which, for example, may be made of a cellulose acetate or polypropylene material. The control body 202 of the depicted implementation may comprise a housing 208 that includes an opening 209 defined on one end thereof, a flow sensor 211 (e.g., a puff sensor or pressure switch), a control component 212 (e.g., a microprocessor, individually or as part of a microcontroller, a printed circuit board (PCB) that includes a microprocessor and/or microcontroller, etc.), a power source 214 (e.g., a battery, which may be rechargeable, and/or a rechargeable supercapacitor), and an end cap that, in some implementations, may include an indicator 216 (e.g., a light emitting diode (LED)).

In the depicted implementation, the control body 202 includes a resonant transmitter and is configured to receive a plurality of substrate tablets 210, each of which includes a resonant receiver (e.g., one or more susceptor components), which together facilitate heating of at least a portion of a substrate tablet (e.g., the substrate material of the substrate tablet). Although in various implementations the resonant transmitter and/or the resonant receiver may take a variety of forms, in the particular implementation depicted in FIG. 4, the resonant transmitter comprises an induction coil 218 that, in some implementations may surround a support cylinder 219, although in other implementations there need not be a support cylinder. In various implementations, the resonant transmitter may be made of one or more conductive materials, including, for example, silver, gold, aluminum, brass, zinc, iron, nickel, and alloys of thereof, conductive ceramics e.g., yttrium-doped zirconia, indium tin oxide, yttrium doped titanate, etc, and any combination of the above. In the illustrated implementation, the induction coil 218 is made of a conductive metal material, such as copper. In further implementations, the induction coil may include a non-conductive insulating cover/wrap material. Such materials may include, for example, one or more polymeric materials, such as epoxy, silicon rubber, etc., which may be helpful for low temperature applications, or fiberglass, ceramics, refractory materials, etc., which may be helpful for high temperature applications. In the depicted implementation, the aerosol delivery device 200 defines a receiving compartment 220, which is configured to receive the plurality of substrate tablets 210 and is defined proximate the opening 209 of the control body 202. As noted above, in other implementations the receiving compartment may be configured to receive a single substrate tablet, and in still other implementations, the same receiving compartment may be configured to receive either a single substrate tablet or multiple substrate tablets. As also noted above, in various implementations the shape of the receiving compartment may be configured to accommodate one or more different profile shapes of a substrate tablet.

In the depicted implementation, the resonant transmitter 218 extends proximate an engagement end of the housing 208, and may be configured to substantially surround at least a portion of the receiving compartment 220. In the depicted implementation, the induction coil 218 defines a generally tubular configuration. In some implementations, the support cylinder 219 may also define a tubular configuration and may be configured to support the induction coil 218 such that the induction coil 218 does not contact with the substrate tablets. As such, the support cylinder 219 may comprise a nonconductive material, which may be substantially transparent to an oscillating magnetic field produced by the induction coil 218. In various implementations, the induction coil 218 may be imbedded in, or otherwise coupled to, the support cylinder 219. In the illustrated implementation, the induction coil 218 is engaged with an outer surface of the support cylinder 219; however, in other implementations, the coil may be positioned at an inner surface of the support cylinder, be fully imbedded in the support cylinder, or have some other configuration.

In many respects, the aerosol delivery device 200 of FIG. 4 may have similar components or similar component variations as the aerosol delivery device 100 of FIG. 2. As such, reference is made to the discussions above regarding these components and component variations, which will not be repeated here. As noted above, the aerosol delivery device 200 of the depicted implementation is configured to receive a plurality of susceptor tablets 210. Although other configurations are possible, the device 200 of the depicted implementation is configured to receive as few as one and as many as six (or more) substrate tablets 210. It should be noted that in the depicted implementation, the spacing between substrate tablets 210 has been exaggerated for ease of depiction. Thus, in some implementations the substrate tablets may be positioned such that an end of one tablet is directly proximate (such as, for example, contacting) an end of the adjacent tablet. In other implementations, however, the device (such as, but not limited to, the receiving compartment of the device) may be configured such that spacing exists between adjacent substrate tablets.

Figure 5A:
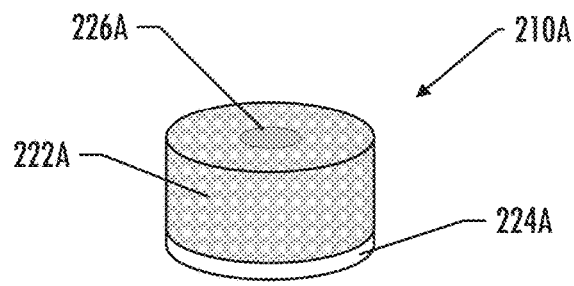
Figure 5B:
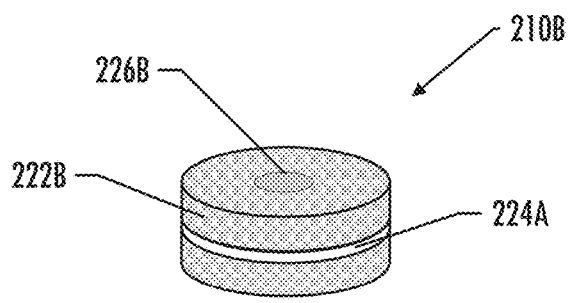
Figure 5C:
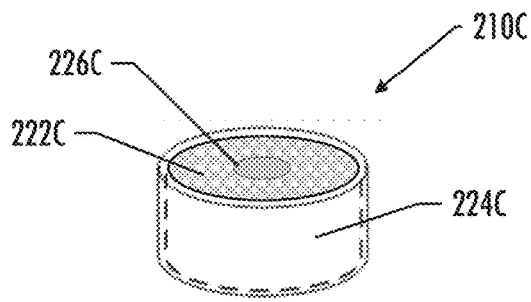

FIGS. 5A-5C show three non-limiting examples of substrate tablets 210A, 210B, and 210C, according some example implementations of the present invention. In some implementations, the substrate tablets of FIGS. 5A-5C may be used in conjunction with an aerosol delivery device (such as the aerosol delivery device 200 of FIG. 4) configured for use with a plurality of substrate tablets. Although other implementations may differ, in the implementations depicted in FIGS. 5A-5C the substrate tablets 210A, 210B, 210C comprise granular substrate materials 222A, 222B, 222C that are combined with substantially solid susceptor components 224A, 224B, 224C. As will be described in more detail below, the susceptor components 224A, 224B, 224C are configured to be heated by the resonant transmitter of the control body.

The substrate material 222A, 222B, and 222C of the depicted implementations may comprise a tobacco material, a non-tobacco material, or a combination thereof. As such, reference is made to the substrate materials and additives (and variations thereof), which will not be repeated here.

FIG. 5A illustrates a substrate tablet 210A comprising a granulated substrate material 222A (which may include any one or any combination of substrate materials described above) and a substantially solid susceptor component 224A, which are together formed into a tablet. Although other sizes and shapes are possible, in the depicted implementation the substrate tablet 210A has a substantially circular profile shape (e.g., as viewed from the top of FIG. 5A) that forms a substantially cylindrical overall shape. The substrate tablet 210A of the depicted implementation also includes a single tablet passage 226A configured to allow air and/or aerosol flow therethrough. In the depicted implementation, the substantially solid susceptor component 224A comprises a susceptor ring located proximate one of the end surfaces of the substrate tablet 210A. It should be noted that in other implementations, the susceptor component may have other shapes, and need not have a round shape. In some implementations, one or more surfaces of the susceptor component may have a surface treatment (e.g., a surface texture) and/or a coating to facilitate combining the substrate material with the susceptor component. In some implementations, the susceptor component need not have a solid shape. For example, in some implementations the susceptor component may comprise a mesh. For example, in some implementations the susceptor ring may comprise a mesh ring.

As noted above, the susceptor component 224A of the depicted implementation may be made of a susceptor material. In some implementations, the susceptor material may include a ferromagnetic material including, but not limited to, cobalt, iron, nickel, zinc, manganese, and any combinations thereof. In other implementations, the susceptor material may comprise other materials, including, for example, other metal materials such as aluminum or stainless steel, as well as ceramic materials such as silicon carbide, carbon materials, and any combinations of any of the materials described above. In still other implementations, the susceptor material may comprise other conductive materials including metals such as copper, alloys of conductive materials, or other materials with one or more conductive materials imbedded therein.

FIG. 5B illustrates a substrate tablet 210B of another example implementation comprising a granulated substrate material 222B (which may include any one or any combination of substrate materials described above) and a substantially solid susceptor component 224B, which are together formed into a tablet. Although other sizes and shapes are possible, in the depicted implementation the substrate tablet 210B has a substantially circular profile shape (e.g., as viewed from the top of FIG. 5B) that forms a substantially cylindrical overall shape. The substrate tablet 210B of the depicted implementation also includes a single tablet passage 226B configured to allow air and/or aerosol flow therethrough. In the depicted implementation, the substantially solid susceptor component 224B comprises a susceptor ring located between the end surfaces of the substrate tablet 210B. Although in various implementations the substrate ring may be located in any location of the substrate tablet, in the depicted implementation the substrate ring is located approximately half way between the end surfaces of the substrate tablet 210B. As noted above, the susceptor component 224B of the depicted implementation may be made of any one or any combinations of susceptor materials, including any one or any combination of those example susceptor materials described above.

FIG. 5C illustrates a substrate tablet 210C of another example implementation comprising a granulated substrate material 222C (which may include any one or any combination of substrate materials described above) and a substantially solid susceptor component 224C, which together are formed into a tablet. Although other sizes and shapes are possible, in the depicted implementation the substrate tablet 210C has a substantially circular profile shape (e.g., as viewed from the top of FIG. 5C) that forms a substantially cylindrical overall shape. The substrate tablet 210C of the depicted implementation also includes a single tablet passage 226C configured to allow air and/or aerosol flow therethrough. In the depicted implementation, the substantially solid susceptor component 224C an open-ended cup defining a cavity therein, wherein the granulated substrate material 222C is located in the cavity. Although in various implementations the substrate material may fill any portion of the cavity, in the depicted implementation the substrate material fills substantially all of the cavity (with the exception of the tablet passage 226C). As noted above, the susceptor component 224C of the depicted implementation may be made of any one or any combinations of susceptor materials, including any one or any combination of those example susceptor materials described above.

Figure 6:
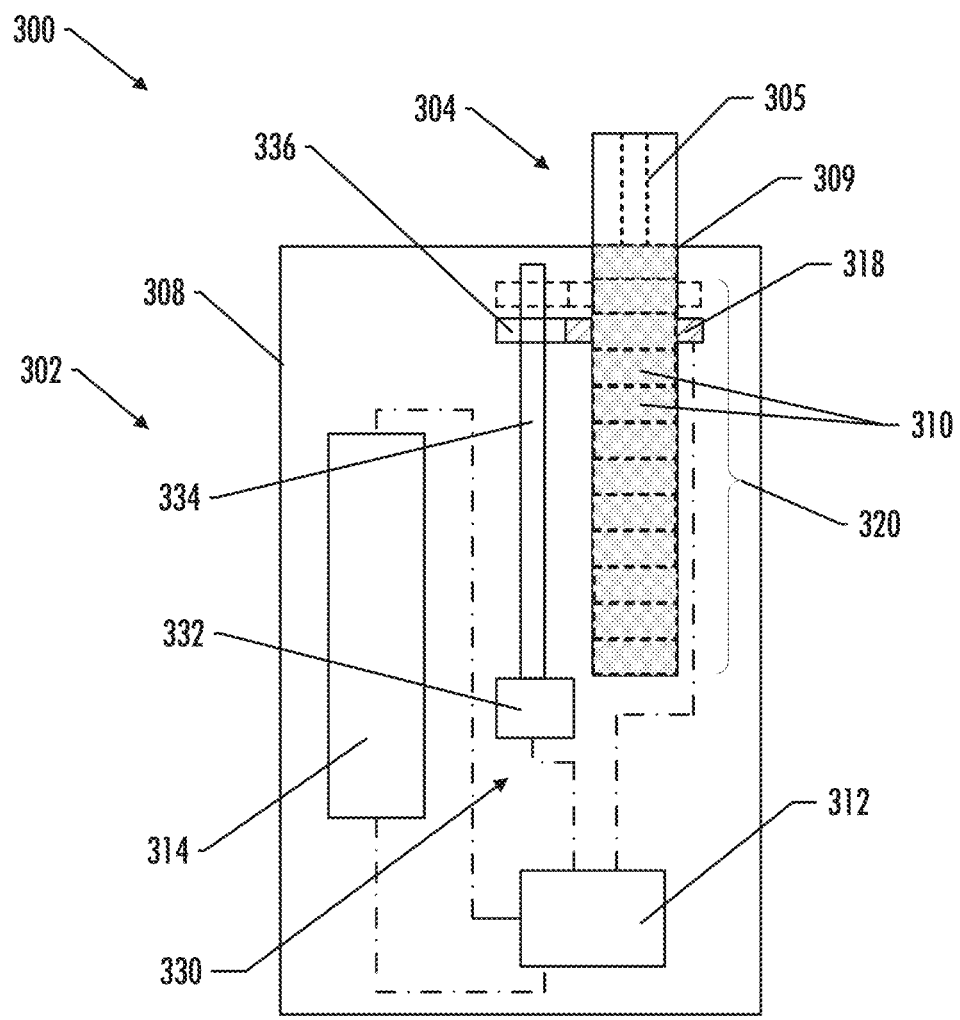

In some implementations, an aerosol delivery device of the present invention may be configured to use segmented heating to inductively heat, separately, one or more individual tablets received therein. A schematic illustration of an example implementation of an aerosol delivery device 300 in accordance with the present disclosure is shown in FIG. 6. In general, the aerosol delivery device 300 includes a mouthpiece portion 304 that is attachable and removable from a control body 302. In the depicted implementation, the mouthpiece portion 304 includes an aerosol passage 305 disposed therethrough. Although not included in the depicted implementation, in some implementations the mouthpiece portion may include a filter, as described above. The control body 302 of the depicted implementation may comprise a housing 308 that includes an opening 309 defined on one end thereof, a flow sensor (not shown), a control component 312 (e.g., a microprocessor, individually or as part of a microcontroller, a printed circuit board (PCB) that includes a microprocessor and/or microcontroller, etc.), and a power source 314 (e.g., a battery, which may be rechargeable, and/or a rechargeable supercapacitor). In some implementations, the aerosol delivery device may also include an indicator, as described above.

In the depicted implementation, the control body 302 includes a resonant transmitter 318 and is configured to receive a plurality of substrate tablets 310, each of which includes a resonant receiver (e.g., one or more susceptor components), which together facilitate heating of at least a portion of a substrate tablet (e.g., the substrate material of a substrate tablet). In various implementations the resonant transmitter and/or the resonant receiver may take a variety of forms. In some implementations, for example, the resonant transmitter may comprise an induction coil, however, other transmitters are possible. As will be described in more detail below, in the depicted implementation the resonant transmitter 318 is configured to be positioned proximate individual substrate tablets 310 received in the device 300. In other implementations, the resonant transmitter may be positioned proximate a group of substrate tablets. In various implementations, the resonant transmitter may be made of one or more conductive materials, including, for example, silver, gold, aluminum, brass, zinc, iron, nickel, and alloys of thereof, conductive ceramics e.g., yttrium-doped zirconia, indium tin oxide, yttrium doped titanate, etc, and any combination of the above. In the illustrated implementation, the resonant transmitter 318 is made of a conductive metal material, such as copper. In further implementations, the helical coil may include a non-conductive insulating cover/wrap material. Such materials may include, for example, one or more polymeric materials, such as epoxy, silicon rubber, etc., which may be helpful for low temperature applications, or fiberglass, ceramics, refractory materials, etc., which may be helpful for high temperature applications. In the depicted implementation, the aerosol delivery device 300 defines a receiving compartment 320, which is configured to receive a plurality of substrate tablets 310 and is defined proximate the opening 309 of the control body 302. As noted above, in other implementations the receiving compartment may be configured to receive a single substrate tablet, and in still other implementations, the receiving compartment may be configured to receive either a single substrate tablet or multiple substrate tablets. As also noted above, in various implementations the shape of the receiving compartment may be configured to accommodate one or more different profile shapes of a substrate tablet.

In some respects, the aerosol delivery device 300 of FIG. 4 may have similar components or similar component variations as the aerosol delivery device 100 of FIG. 2. As such, reference is made to the discussions above regarding these components and component variations, which will not be repeated here.

As noted above, the aerosol delivery device 300 of the depicted implementation is configured to receive a plurality of susceptor tablets 310. Although other configurations are possible, the device 300 of the depicted implementation is configured to receive as few as one and as many as twelve (or more) substrate tablets 310. In the depicted implementation, the substrate tablets are positioned such that an end of one tablet is directly proximate (such as, for example, contacting) an end of the adjacent tablet. In other implementations, however, the device (such as, but not limited to, the receiving compartment of the device) may be configured such that spacing exists between adjacent substrate tablets.

It should be noted that while the aerosol delivery device of FIG. 6 is shown as having a substantially rectangular or fob-shaped control body 302 for ease of illustration, in other implementations the control body may have any other shape including an elongated shell or body that may be substantially tubular in shape and, as such, resemble the shape of a conventional cigarette or cigar, and thus the components described below may be sized and configured to fit inside an elongated body.

In some implementations, a separate component may be used to facilitate the loading and positioning multiple substrate tablets into an aerosol delivery device. For example, some implementations may include a rack or tray configured to hold multiple substrate tablets, and that is configured to be loaded into an aerosol delivery device. For example, in some implementations a substrate tablet rack or tray may slide into and out of an aerosol delivery device to facilitate loading and positioning of one or more substrate tablets.

In various implementations, an aerosol delivery device of the present invention may be configured to separately heat a plurality of substrate tablets contained in the device. This may be accomplished in a variety of ways. For example, in some implementations (such as the depicted implementation) a resonant transmitter may be moved relative to a plurality of relatively stationary substrate tablets. In other implementations, substrate tablets may be moved relative to a relatively stationary resonant transmitter. In other implementations, both the resonant transmitter and the substrate tablets may move relative to each other. In still other implementations, the resonant transmitter and substrate tablets may be relatively stationary and the control component may control one or more portions of the resonant transmitter to separately heat the substrate tablets contained in the device. In some implementations, the inductive heating arrangement may be configured to heat different substrate tablets at different times. In such a manner, the inductive heating arrangement may provide segmented heating of the substrate tablets. For example, in some implementations the inductive heating arrangement of the present invention may be configured to heat a first substrate tablet and then, subsequently, heat a second substrate tablet. In such a manner, the inductive heating arrangement may be configured to progressively heat the substrate tablets. In other implementations, the inductive heating arrangement may be configured to heat individual or multiple substrate tablets at the same time, or the inductive heating arrangement may be configured to heat one or more of a plurality of substrate tablets. Some examples of control methods configured to provide segmented heating are described in U.S. patent application Ser. No. 15/976,526, titled *Control Component for Segmented Heating in an Aerosol Delivery Device*, which is incorporated herein by reference in its entirety. In still other implementations, there may be multiple independent resonant transmitters (such as, for example, multiple independent coils, each of which may be individually activated. In such a manner, each independent resonant transmitter may be located proximate, or may be indexed or moved proximate, an individual substrate tablet.

In the depicted implementation, the aerosol delivery device 300 includes an indexing mechanism 330 that is configured to move a resonant transmitter 318 (which may be, in some implementations, a coil) relative to the substrate tablets 310. In various implementations, the indexing mechanism 330 may be coupled to the resonant transmitter 318 and may be configured to generate incremental relative motion between the resonant transmitter 318 and the substrate tablets 310. In the depicted implementation, the indexing mechanism 330 is coupled to the resonant transmitter 318 such that the indexing mechanism 330 moves the resonant transmitter 318 through a series of incremental heating positions so as to incrementally heat a corresponding series of substrate tablets 310. Although other configurations are possible, in the depicted implementation the indexing mechanism 330 comprises a small motor 332 (e.g., a micro stepping motor) configured to rotate a lead screw 334. Further, a carrier 336, to which the resonant transmitter 318 is affixed, is threaded through the lead screw 334. In such a manner, rotation of the lead screw 334 by the stepper motor 332 may therefor move the carrier 336, and thus the heating member 336, in a substantially linear fashion. In various implementations, the characteristics (including for example, the dimensions and/or specifications and/or control features) of the control component, stepper motor, lead screw, and carrier may be designed in order to meet a variety of performance objectives. For example, in the implementation depicted in FIG. 6, the indexing mechanism 330 is configured such that the resonant transmitter 318 is moved through a series of discrete positions relative to the plurality of substrate tablets 310. These positions correspond to the positions of the plurality of substrate tablets 310. As such, the control component 312, stepper motor 332, lead screw 334, carrier 336, and resonant transmitter 318 are configured such that the resonant transmitter 318 may be controlled to separately heat each of the substrate tablets 310. In other implementations, a single resonant transmitter may have any number of discrete positions corresponding to any number of substrate tablets.

In some implementations, movement of the induction coil may be initiated by the puffing action of the user through use of one or more various sensors, as otherwise described herein, and/or may be initiated once the puff is discontinued as sensed by one or more various sensors. As noted, in other implementations the device may include an input element (such as, but not limited to, one or more buttons) that may be used to effect movement of the induction coil. In other implementations, a combination of one or more sensors and one or more input elements may be used. In still other implementations, the indexing of the heating member may be manually controlled by a user such that the induction coil may be manually advanced by the consumer. Some examples of mechanisms configured to provide segmented heating are described in U.S. Pat. App. Pub. No. 2019/0289908 to Worm et al., which is incorporated by reference herein in its entirety.

It should be noted that although the control body and the substrate tablet(s) of the present disclosure may be provided together as a complete aerosol delivery device generally, the components may also be provided separately. Accordingly, any discussion otherwise provided herein in relation to the components in combination should also be understood as applying to the control body and the substrate tablet(s) as individual and separate components. The present disclosure also encompasses a disposable unit for use with a reusable unit. In specific implementations, such a disposable unit (which may, in some implementations, be the substrate tablet(s)) can be configured to be received into a reusable unit (which may, in some implementations, be the control body). In other implementations, both units may be disposable. For example, in specific implementations both the control body and the substrate tablet(s) may be disposable.

In another aspect, the present disclosure may be directed to kits that provide a variety of components as described herein. For example, a kit may comprise a control body with one or more substrate tablets. A kit may further comprise a control body with one or more charging components. A kit may further comprise a control body with one or more power sources. A kit may further comprise a control body with one or more substrate tablets and one or more charging components and/or one or more power sources. In further implementations, a kit may comprise a plurality of substrate tablets. A kit may further comprise a plurality of substrate tablets and one or more power sources and/or one or more charging components. The inventive kits may further include a case (or other packaging, carrying, or storage component) that accommodates one or more of the further kit components. The case could be a reusable hard or soft container. Further, the case could be simply a box or other packaging structure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. An aerosol delivery device comprising:
a control body having a housing;
a mouthpiece portion located proximate the housing;
a resonant transmitter located in the control body;
a control component configured to drive the resonant transmitter; and
at least one substrate tablet receivable in the device,
wherein the substrate tablet comprises a granular substrate material and a susceptor component, wherein the substrate material and the susceptor component are formed together, wherein the susceptor component is configured to be heated by the resonant transmitter,
wherein the susceptor component is a single structure comprising one of a susceptor ring or open-ended cup defining a cavity therein,
wherein the substrate tablet defines a peripheral surface, and wherein a plurality of passages are defined around the peripheral surface.

2. The aerosol delivery device of claim 1, wherein the substrate tablet is formed by pressing the substrate material and the susceptor component together.

3. The aerosol delivery device of claim 2, wherein the substrate tablet is formed using a process selected from the group consisting of wet granulation, dry granulation, and direct compression.

4. The aerosol delivery device of claim 1, wherein the substrate tablet defines a profile shape, and wherein the profile shape of the substrate tablet is substantially round.

5. The aerosol delivery device of claim 1, wherein the substrate tablet defines a first end surface and a second end surface, and further includes one or more passages extending from the first end surface to the second end surface.

6. The aerosol delivery device of claim 1, wherein the substrate tablet defines a first end surface and a second end surface, and wherein the susceptor component comprises a susceptor ring located proximate one of the first or second end surfaces.

7. The aerosol delivery device of claim 1, wherein the substrate tablet defines a first end surface and a second end surface, and wherein the susceptor component comprises a susceptor ring located between the first and second end surfaces.

8. The aerosol delivery device of claim 1, wherein the substrate material includes an aerosol precursor composition.

9. The aerosol delivery device of claim 1, wherein the susceptor component comprises a material selected from a cobalt material, an iron material, a nickel material, a zinc material, a manganese material, a stainless steel material, a ceramic material, a silicon carbide material, a carbon material, and combinations thereof.

10. The aerosol delivery device of claim 1, wherein the control body is configured to receive multiple substrate tablets.

11. The aerosol delivery device of claim 10, wherein the resonant transmitter is configured to separately heat respective susceptor components of the multiple substrate tablets.

12. The aerosol delivery device of claim 10, wherein the resonant transmitter is configured to heat multiple respective susceptor components of the multiple substrate tablets.

13. The aerosol delivery device of claim 10, wherein each of the multiple substrate tablets includes an aerosol precursor composition, and wherein at least two of the multiple substrate tablets have different levels of aerosol precursor composition.

14. The aerosol delivery device of claim 10, wherein at least two of the multiple substrate tablets have different types of susceptor components.

15. The aerosol delivery device of claim 10, wherein at least two of the multiple substrate tablets have different shapes.

16. A substrate tablet for use with an inductively-heated aerosol delivery device, the substrate tablet comprising:
   a granular substrate material; and
   a susceptor component,
      wherein the substrate material and the susceptor component are formed together,
      wherein the susceptor component is a single structure comprising one of a susceptor ring or open-ended cup defining a cavity therein,
      wherein the tablet defines a peripheral surface, and wherein a plurality of passages are defined around the peripheral surface.

17. The substrate tablet of claim 16, wherein the substrate tablet is formed by pressing the substrate material and the susceptor component together.

18. The substrate tablet of claim 17, wherein the substrate tablet is formed using a process selected from the group consisting of wet granulation, dry granulation, and direct compression.

19. The substrate tablet of claim 16, wherein the tablet defines a profile shape, and wherein the profile shape of the tablet is substantially round.

20. The substrate tablet of claim 16, wherein the tablet defines a first end surface and a second end surface, and further includes one or more passages extending from the first end surface to the second end surface.

21. The substrate tablet of claim 16, wherein the tablet defines a first end surface and a second end surface, and wherein the susceptor component comprises a susceptor ring located proximate one of the first or second end surfaces.

22. The substrate tablet of claim 16, wherein the tablet defines a first end surface and a second end surface, and wherein the susceptor component comprises a susceptor ring located between the first and second end surfaces.

23. The substrate tablet of claim 16, wherein the substrate material includes an aerosol precursor composition.

24. The substrate tablet of claim 16, wherein the susceptor component comprises a material selected from a cobalt material, an iron material, a nickel material, a zinc material, a manganese material, a stainless steel material, a ceramic material, a silicon carbide material, a carbon material, and combinations thereof.

* * * * *